United States Patent [19]

Sagredos et al.

[11] Patent Number: 5,594,327
[45] Date of Patent: Jan. 14, 1997

[54] METHOD FOR DETERMINING THE DEGREE OF DETERIORATION OF OILS OR FATS USED FOR FRYING FOODS

[75] Inventors: Angelos N. Sagredos, Hamburg; Ilmar Neumeister, Groebenzell, both of Germany

[73] Assignee: Wamsler Grosskuechentechnik GmbH, Munich, Germany

[21] Appl. No.: 297,000

[22] Filed: Aug. 26, 1994

[30] Foreign Application Priority Data

Aug. 27, 1993 [DE] Germany ............................ 43 28 966.5

[51] Int. Cl.$^6$ ............................ G01N 27/06; G01N 33/03; G01N 33/28
[52] U.S. Cl. ............................ 324/71.1; 324/439; 324/693; 324/698; 436/60; 436/150
[58] Field of Search ............................ 324/71.1, 439, 324/444, 446–450, 691, 693, 694, 696, 698, 722; 204/153.1, 400; 340/603, 660, 664; 436/60, 150

[56] References Cited

U.S. PATENT DOCUMENTS

| | | |
|---|---|---|
| 4,372,980 | 2/1983 | Luebke et al. ............................ 426/231 |
| 4,764,258 | 8/1988 | Kauffman ............................ 436/60 X |
| 5,071,527 | 12/1991 | Kauffman ............................ 324/439 |
| 5,089,780 | 2/1992 | Megerle ............................ 324/448 |
| 5,239,258 | 8/1993 | Kauffman ............................ 324/71.1 |
| 5,331,287 | 7/1994 | Yamagishi et al. ............................ 324/446 |
| 5,339,254 | 8/1994 | Matlock et al. ............................ 364/499 |
| 5,463,321 | 10/1995 | Matlock et al. ............................ 324/439 |
| 5,518,590 | 5/1996 | Fang ............................ 324/71.1 X |
| 5,523,692 | 6/1996 | Kuroyanagi et al. ............................ 324/438 |

FOREIGN PATENT DOCUMENTS 0501682   9/1992   European Pat. Off. .

OTHER PUBLICATIONS

Hadorn et al., "For Determination of The Oxidation Stability Of Oils and Fats", vol. 70:57–65, (1974) Month unavailable.

Hindrich, "For Investigation Of Used Frying Fats," vol. 69:461–466, (1973) month unavailable.

Patent Abstracts of Japan, vol. 12, No. 477 (P–800), Dec. 14, 1988 and JP–A–63 195 555, published Aug. 12, 1988.

*Primary Examiner*—Kenneth A. Wieder
*Assistant Examiner*—Glenn W. Brown
*Attorney, Agent, or Firm*—Foley & Lardner

[57] ABSTRACT

A method for determining the degree of deterioration of oils or fats for deep-frying or frying foods is disclosed. The specific ohmic resistance of the oils or fats is measured and the extent of the fall of this resistance with increasing deep-frying time or frying time is used as a correlation for the degree of deterioration of the oils or fats.

18 Claims, 2 Drawing Sheets

METHOD FOR DETERMINING THE DEGREE OF DETERIORATION OF OILS OR FATS USED FOR FRYING FOODS

BACKGROUND OF THE INVENTION

1. Field of the Invention

The present invention relates to a method for the determination of the degree of deterioration of oils or fats used for frying foods.

2. Description of Related Art

For determining the degree of deterioration of oils and fats for frying foods, it is known to measure the dielectric constants of the heated oils or fats or, after addition of reagents, the color change thereof in the course of time.

The measured values to be determined by these methods have frequently proven to be unreliable, usually require a comparison oil or a comparison fat, and are complex in terms of apparatus used and amount of time-consumed.

The German journal "Deutsche Lebensmittel-Rundschau", volume 69, part 12, 1973, pages 461 to 466 discloses a method for determining the degree of deterioration of oils and fats for frying, in which the content of oxidized fats is used as a criterion.

The German journal "Deutsche Lebensmittel-Rundschau", volume 70, part 2, 1974, pages 57 to 65 and EP 0,501,682 A2 disclose determining the keeping quality or stability to oxidation of oils or fats by means of conductometric measurement cells.

SUMMARY OF THE INVENTION

One object of the present invention is to provide a method which leads to reliable measured values, does not require comparison oils or comparison fats and can be carried out without great complexity in terms of apparatus and with a relatively low expenditure of time.

In accomplishing the foregoing objects, there has been provided according to one aspect of the present invention, a method for determining the degree of deterioration of oils or fats used in a food frying process. The method includes, measuring the specific electrical resistance of the oils or fats, and using a first correlation between the change in the resistance and the amount of frying time and a second correlation between the electrical resistance and amount of deterioration to determine the amount of deterioration of the fat or oils.

In one embodiment of the present invention, the first correlation is based on the difference in the electrical resistance of the fat or oil between any time prior to the first use of the fat or oil in the frying process and at least one predetermined time point after the first frying.

In another embodiment of the present invention, the first correlation is based on the difference in the electrical resistance of the fat or oil between a first predetermined time point, preferably about 4 to about 16 hours, after a first use of the oil or fat in the frying process and at least one additional time point after the first predetermined time point.

Further objects, features and advantages of the present invention will become apparent from the detailed description of the preferred embodiments which follows.

DETAILED DESCRIPTION OF THE PREFERRED EMBODIMENTS

Figure 1:
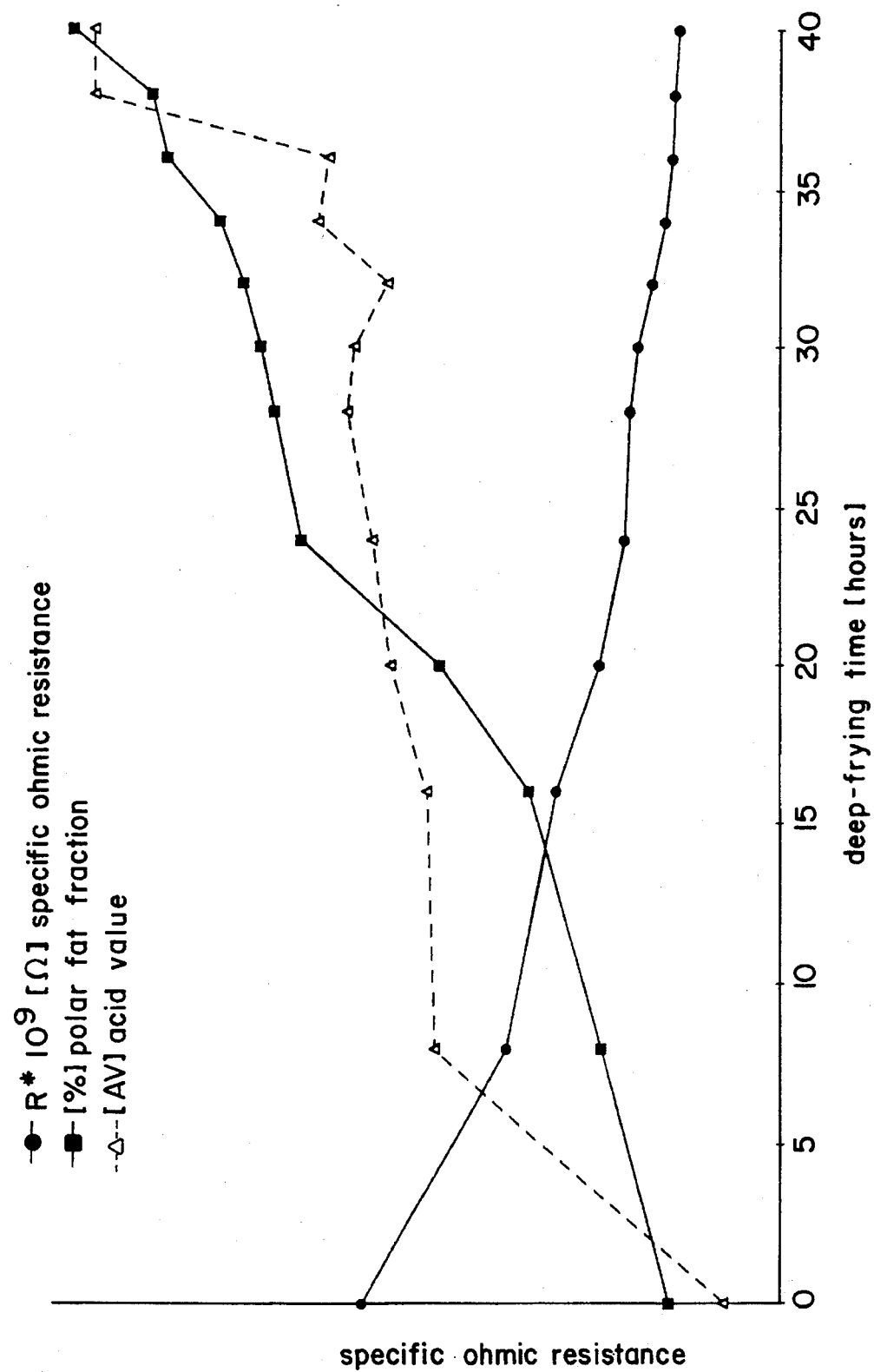
FIG. 1 is a graphical representation of the change of specific ohmic resistance, percent polar fat fraction and acid value with respect to increased frying time.
Figure 2:
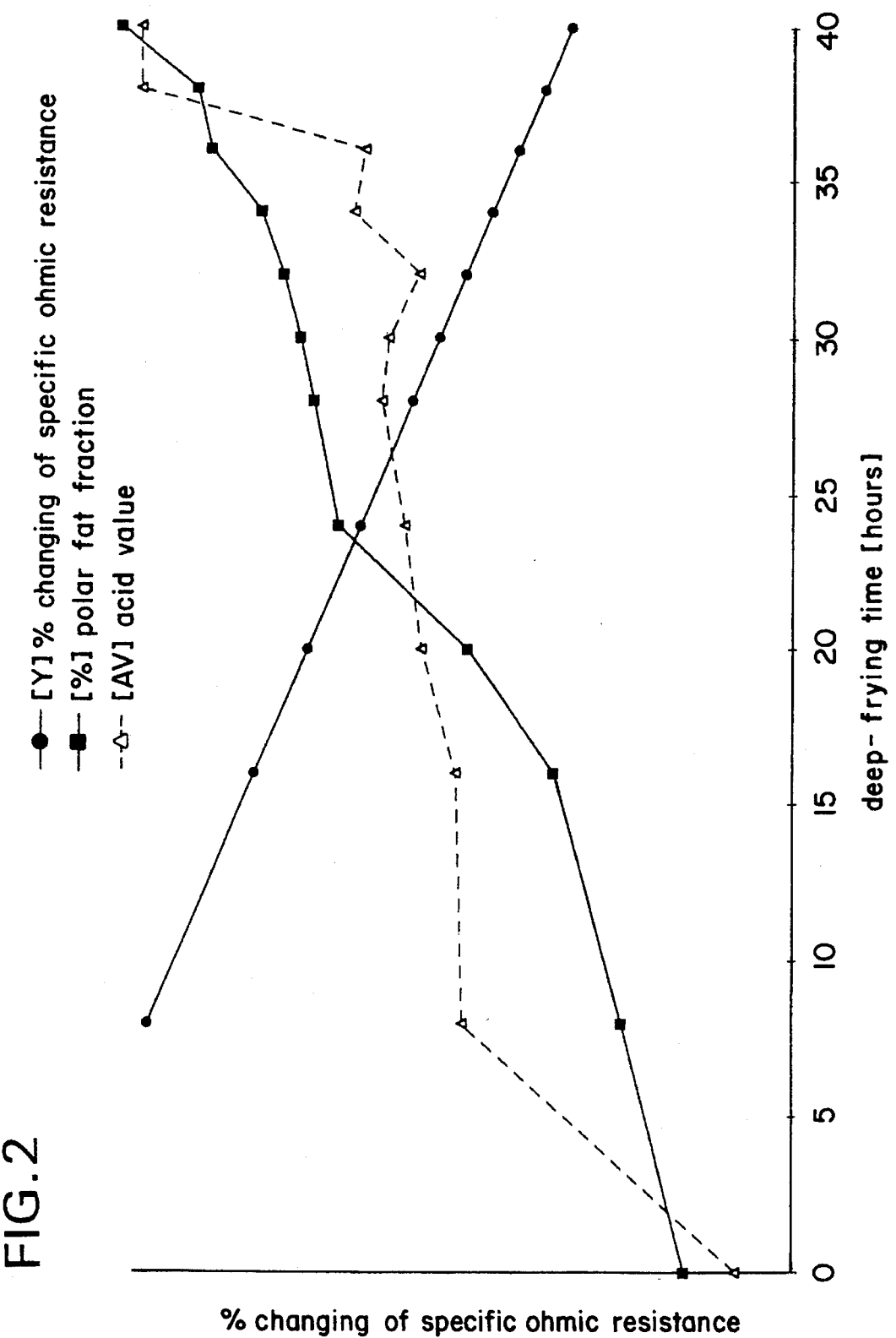
FIG. 2 is a graphical representation of the percentage change of specific ohmic resistance relative to 8 hours frying time with respect to the fat deterioration indicated through the buildup of fatty acid and polar fat fractions.

The present invention discloses a method which includes measuring the specific ohmic resistance of the oils or fats, and using the extent of the change of this resistance with increasing frying time as a correlation for the degree of deterioration of the oils or fats. In the present invention, frying is defined as deep-frying or any other frying process, such as pan frying, where hot oils or fats are used to cook the food product.

No comparison oil or comparison fat is required if the correlation used is the difference in the resistances between any time prior to the first frying and the particular time point after the first deep-frying or frying. Also, no comparison fat or oil is required if the correlation used is the difference in the resistances between a first predetermined time point—preferably 4 to 16 hours—after a first frying and a particular time point after the first predetermined time point.

The first predetermined time point embodiment is dependent on the type of the particular oil or fat used, and, once the first predetermined time point has been appropriately determined, a correlation can be established such that after this time point the fall of the resistance difference is linear or permits a linear interpolation. The linear function can be represented graphically in a diagram, for example on a video screen, which makes it possible for the user to extrapolate to a time point to which the oil or fat is degraded or at any rate may no longer be used—according to food regulations.

The linear function can also be represented by the slope-intercept equation of a straight line. The measurement of the specific ohmic resistance is equivalent to the measurement of the specific conductivity, and also to the measurement of the resistance or the conductivity between the electrodes of the particular measurement instrument used.

Measurement of the degree of deterioration of a deep-frying fat or frying fat with the specific resistance or conductivity

EXAMPLE 1

The specific resistance R is the ohmic resistance of a liquid in a measurement cell, which cell is characterized by the cell constant c as the ratio of electrode spacing d (cm) to electrode surface area F (cm$^2$)

$$c = \frac{d}{F} \text{ (cm}^{-1}\text{)}.$$

From the value of R and the cell constant c the conductivity L of the deep-frying fat can be calculated by the formula $$L = \frac{c}{R} \text{ (ohm}^{-1} \cdot \text{cm}^{-1}\text{)}.$$

The electrical conductivity of fats and oils is very low. It is in the region of approximately $L = 10^{-12}$ ohm$^{-1} \cdot$ cm$^{-1}$. Because of this low conductivity, an instrument was used which can indicate resistances up to $2 \cdot 10^{14}$ ohm for the measurements of the specific resistance.

A measurement cell for liquids having a cell constant $c=0.114$ $cm^{-1}$ and two flat platinum electrodes of approximately 2 $cm^2$ surface area at a distance of approximately 0.2 cm were connected to a megohmeter. The measurement voltage was set to 100 V direct current. The deep-frying fat to be tested was heated in a 20 mm diameter test tube in a heating block to a constant temperature of 75° C. The resistance R in ohms of three individual aliquots per sample was measured approximately 1 min after applying the voltage and the mean was then calculated. Test tube and measurement cell were cleaned prior to each measurement with a solvent such as petroleum ether.

Under these measurement conditions, the degree of deterioration of completely refined soybean oil was measured in the deep-frying of fish sticks. The fatty acid composition of the most important fatty acids of the soybean oil was as follows:

Palmitic acid (16 carbon atoms: 0 double bonds) (C16:0))= 10.9%
Stearic acid (C18:0)=3.9%
Oleic acid and oleic acid isomers (C18: 1)=22.2%
Linoleic acid and linoleic acid isomer8 (C18:2)=53.6%

The deep-frying temperature was 175° C.

The measured values of specific resistance and the conductivity calculated therefrom and the measured values of the polar fractions and of the acid value are summarized in Table 1 below:

TABLE 1

| Deep-frying time [h] | Specific resistance $R \times 10^9$ [$\Omega$] | Conductivity $S \times 10^{-12}$ [$\Omega^{-1} \cdot cm^{-1}$] | Degree of deterioration Polar fat fraction* [%] | Acid value** [AV] |
|---|---|---|---|---|
| 0 | 14.39 | 7.92 | 3.8 | 0.16 |
| 8 | 9.39 | 12.14 | 6.1 | 0.95 |
| 16 | 7.65 | 14.90 | 8.6 | 0.97 |
| 20 | 6.17 | 18.47 | 11.7 | 1.07 |
| 24 | 5.29 | 21.55 | 16.4 | 1.12 |
| 28 | 5.12 | 22.26 | 17.3 | 1.19 |
| 30 | 4.85 | 23.50 | 17.8 | 1.17 |
| 32 | 4.36 | 26.14 | 18.4 | 1.08 |
| 34 | 3.91 | 29.15 | 19.2 | 1.27 |
| 36 | 3.67 | 31.06 | 21.0 | 1.24 |
| 38 | 3.60 | 31.66 | 21.5 | 1.88 |
| 40 | 3.46 | 32.95 | 24.2 | 1.88 |

*Determined by the DGF (German fat research association) standard method C-III 3 b.
**Determined by the DGF standard method C-V 2.

The specific resistance of the soybean oil was decreased by the deep-frying of fish sticks and a linear dependence (correlation) was shown between the measured values of ohmic resistance and the deterioration of soybean oil, which was characterized through the measured increase of the polar fractions and the acidic value. The deep-frying fat, according to the polar fractions, had only deteriorated after 40 hours. The ohmic resistance decreased linearly from $14.39 \cdot 10^9$ $\Omega$ to $3.46 \cdot 10^9$ $\Omega$. Since the conductivity is the reciprocal of the ohmic resistance, a linear increase of conductivity from 7.92 to $32.94 \cdot 10^{-12}$ was observed.

The correlation between the specific resistance and the degree of deterioration of the deep-frying fat was better demonstrated by using the measured value of 8 hours deep-frying time or 16 hours deep-frying time as the reference value, not the measured value of 0 hours deep-frying time (=fresh fat). Subsequent measured values were calculated as relative values.

The calculation of subsequent relative values is carried out by dividing the normalized value of 100% by the quotient of the measured specific resistance which corresponds to the 100% value, divided by the measured specific resistance at the frying time the relative value is being calculated for.

For both series of measurements relative values were thus normalized, and a best-fit line was calculated by the method of least squares (Gauss) (see equation below), characterized by the gradient (slope) +/− error, the axis intercept +/− error and the correlation coefficients. The same calculation method is used after the natural logarithm (base e) was calculated from the measured values of specific resistance.

Best-fit line
y=m•x+b
y=normalized value on the best-fit
line [% freshness]
m=gradient (slope) of the line
x=deep-frying time [hours]
b=y-axis intercept of the line Solving the equation for "y" gives the "% of original or normalized specific resistance remaining" at time "x". The relative values thus calculated (shown as Y) and the normalized values from the linear or the logarithmic regression of the measured values in ohms from the deep-frying of fish sticks in soybean oil are summarized in Table 2 below:

TABLE 2

| | | Relative values and best-fit line [% specific resistance] | | | | | |
|---|---|---|---|---|---|---|---|
| | | 8 hours deep-frying time | | | 16 hours deep-frying time | | |
| Deep-frying time (X) [hours] | Specific resistance $R \times 10^9$ [$\Omega$] | ln. normalized | linear normalized | Y calculated linear | ln normalized | linear normalized | Y calculated linear |
| 0 | 14.39 | | | | | | |
| .8 | 9.39 | 100.00 | 100.00 | 92.8 | — | — | |
| 16 | 7.65 | 90.85 | 81.47 | 77.6 | 100.00 | 100.00 | 91.4 |
| 20 | 6.17 | 81.25 | 65.71 | 70.0 | 89.43 | 80.65 | 83.0 |
| 24 | 5.29 | 74.38 | 56.34 | 62.4 | 81.87 | 69.15 | 74.6 |
| 28 | 5.12 | 72.92 | 54.53 | 54.8 | 80.26 | 66.93 | 66.2 |
| 30 | 4.85 | 70.50 | 51.65 | 51.0 | 77.60 | 63.40 | 62.0 |
| 32 | 4.36 | 65.75 | 46.43 | 47.2 | 72.37 | 56.99 | 57.8 |
| 34 | 3.91 | 60.88 | 41.64 | 43.4 | 67.01 | 51.11 | 53.6 |
| 36 | 3.67 | 58.05 | 39.08 | 39.6 | 63.90 | 47.97 | 49.4 |

TABLE 2-continued

| Deep-frying time (X) [hours] | Specific resistance R × 10⁹ [Ω] | Relative values and best-fit line [% specific resistance] | | | | | |
|---|---|---|---|---|---|---|---|
| | | 8 hours deep-frying time | | | 16 hours deep-frying time | | |
| | | ln. normalized | linear normalized | Y calculated linear | ln normalized | linear normalized | Y calculated linear |
| 38 | 3.68 | 58.17 | 39.19 | 35.8 | 64.03 | 48.10 | 45.2 |
| 40 | 3.46 | 55.42 | 36.85 | 32.0 | 61.00 | 45.23 | 41.0 |
| Gradient (m): | | −1.4 ± 0.05 | −1.9 ± 0.12 | −1.5 ± 0.08 | −2.1 ± 0.14 | | |
| Axis intercept (b): | | 111 ± 1.6 | 108 ± 3.5 | 122 ± 2.4 | 125 ± 4.4 | | |
| Correlation coefficient (r): | | −0.9912 | −0.9780 | −0.9862 | −0.9760 | | |

The values of the correlation coefficients being close to 1.000 clearly confirm the linear decrease of the specific resistance with increasing deep-frying time, and the decrease in quality (Y) of the soy bean oil associated therewith.

EXAMPLE 2

Cod fillet was deep-fried at 175° C. with soy bean oil of the following fatty acid composition.
Palmitic acid (C16:0)=8.1%
Stearic acid (C18:0)=4.9%
Oleic acid and Oleic acid isomers (C18.1)=27.2%
Linoleic acid and linoleic acid isomers (C18:2)=53.3%

The degree of deterioration of this deep-frying fat was measured by means of specific resistance as described in Example 1.

The measured values of the specific resistance and the measured values calculated therefrom of the conductivity and the relative values which are based on the measured values of the deep-frying fat after 8 hours and 16 hours of deep-frying time and have been normalized are summarized in Table 3 below. The comparison values of polar fractions and AV are likewise entered in Table 3.

It is clear from Table 3 that the measured values of the specific resistance and of the conductivity are correlated with the degree of deterioration of the deep-frying fat soybean oil, which degree of deterioration is shown by the increase of the polar fractions and the AV. This correlation is also confirmed by the best-fit line and the correlation coefficients.

The best-fit line is given by the equation (see Example 1):

$$y = m \cdot x + b$$

EXAMPLE 3

Breaded pork cutlet was deep-fried at 175° C. with a deep-frying fat of the following fatty acid composition
Palmitic acid (C16:0)=44.4%
Stearic acid (C18:0)=4.8%
Oleic acid and oleic acid isomers (C18:1)=36.4%
Linoleic acid and linoleic acid isomers (C18:2)=10.3%

The degree of deterioration of this deep-frying fat was measured by means of specific resistance as described in Example 1.

TABLE 3

| Deep-frying time (X) [hours] | Specific resistance R × 10⁹ [Ω] | Conductivity S × 10⁻¹² [Ω⁻¹ × cm⁻¹] | Polar fractions [%] | Acid value [AV] | Relative values [% specific resistance] | | | |
|---|---|---|---|---|---|---|---|---|
| | | | | | 8 hours | | 16 hours | |
| | | | | | linear | log. | linear | log. |
| 0 | 14.39 | 7.92 | 3.8 | 0.05 | — | — | — | — |
| 8 | 8.56 | 13.31 | 7.9 | 0.32 | 100 | 100 | — | — |
| 16 | 5.85 | 19.48 | 13.1 | 0.86 | 68.34 | 82.27 | 100 | 100 |
| 20 | 4.51 | 25.27 | 13.4 | 1.10 | 52.69 | 70.15 | 77.09 | 85.27 |
| 24 | 3.68 | 30.97 | 15.2 | 1.08 | 42.99 | 60.68 | 64.91 | 73.76 |
| 28 | 3.39 | 33.62 | 16.4 | 1.61 | 39.60 | 56.86 | 57.95 | 69.11 |
| 30 | 2.89 | 39.44 | 17.1 | 1.77 | 33.76 | 49.43 | 49.40 | 60.08 |
| 32 | 2.71 | 42.06 | 18.4 | 1.81 | 31.66 | 46.43 | 46.32 | 56.44 |
| 34 | 2.61 | 43.67 | 19.4 | 1.94 | 30.49 | 44.68 | 44.62 | 54.31 |
| 36 | 2.23 | 51.12 | 20.9 | 2.07 | 26.05 | 37.35 | 38.12 | 45.40 |
| 38 | 2.10 | 54.28 | 20.2 | 2.09 | 24.53 | 34.56 | 35.90 | 42.00 |
| 40 | 2.01 | 56.71 | 25.5 | 2.61 | 23.48 | 32.52 | 34.36 | 39.52 |
| Gradient (m) | | | | | −2.1 ± 0.2 | −2.0 ± 0.06 | −2.5 ± 0.1 | −2.4 ± 0.08 |
| Axis intercept (b) | | | | | 102 ± 5.8 | 113 ± 1.8 | 129 ± 5.6 | 135 ± 2.5 |
| Correlation coefficient (r) | | | | | 0.9896 | −0.9949 | 0.9850 | −0.9939 |

The measured values of the specific resistance and the measured values calculated therefrom of the conductivity and the relative values which were based on the measured values of the deep-frying fat after 8 hours and 16 hours of deep-frying time and were normalized are summarized in Table 4 below:

The measured values of the specific resistance and the measured values calculated therefrom of the conductivity and the relative values which were based on the measured values of the deep-frying fat after 8 hours and 16 hours of deep-frying time and were normalized are summarized in Table 5 below:

TABLE 4

| Deep-frying time (X) [hours] | Specific resistance $R \times 10^9$ [$\Omega$] | Conductivity $S \times 10^{-12}$ [$\Omega^- \times cm^{-1}$] | Polar fractions [%] | Acid value [AV] | Relative values [% specific resistance] | | | |
|---|---|---|---|---|---|---|---|---|
| | | | | | 8 hours | | 16 hours | |
| | | | | | linear | log. | linear | log. |
| 0 | 10.10 | 11.28 | 8.6 | 0.54 | — | — | — | — |
| 8 | 8.54 | 13.34 | 9.0 | 0.52 | 100 | 100 | — | — |
| 16 | 7.57 | 15.05 | 14.0 | 0.77 | 88.6 | 94.3 | 100 | 100 |
| 20 | 6.46 | 17.64 | 15.4 | 0.99 | 75.6 | 86.9 | | |
| 24 | 5.44 | 20.95 | 16.7 | 0.86 | 63.7 | 78.9 | 71.8 | 83.6 |
| 28 | 4.52 | 25.22 | 16.7 | 0.90 | 52.9 | 70.3 | 59.7 | 74.5 |
| 30 | 4.34 | 26.26 | 20.1 | 1.14 | 50.8 | 68.4 | 57.3 | 72.5 |
| 32 | 4.18 | 27.27 | 21.0 | 1.58 | 48.9 | 66.6 | 55.2 | 70.6 |
| 34 | 3.70 | 30.81 | 21.3 | 1.57 | 43.3 | 61.0 | 48.8 | 64.6 |
| 36 | 3.45 | 33.04 | 22.1 | 1.61 | 40.4 | 57.7 | 45.5 | 61.1 |
| 38 | 3.42 | 33.33 | 22.3 | 1.87 | 40.0 | 57.3 | 45.1 | 60.7 |
| Gradient (m) | | | | | $-2.1 \pm 0.1$ | $-1.5 \pm 0.07$ | $-2.4 \pm 0.1$ | $-1.7 \pm 0.07$ |
| Axis intercept (b) | | | | | $117 \pm 2.8$ | $115 \pm 1.9$ | $131 \pm 4.4$ | $126 \pm 2.1$ |
| Correlation coefficient (r) | | | | | −0.9885 | −0.9886 | −0.9814 | −0.9918 |

It is clear from Table 4 that the measured values of the specific resistance and of the conductivity are correlated with the degree of deterioration of the deep-frying fat used, which degree of deterioration is expressed by the acid value and the polar fractions. The linear associations between deep-frying fat quality decrease and the measured values are confirmed by the correlation coefficients.

The best-fit line is given by the equation (see Example 1):

$$y = m \cdot x + b$$

EXAMPLE 4

French fries were deep-fried at 175° C. with a deep-frying fat of the following fatty acid composition
Palmitic acid (C16:0)=44.4%
Stearic acid (C18:0)=4.8%
Oleic acid and Oleic acid isomers (C18:1)=36.4%
Linoleic acid and linoleic acid isomers (C18:2)=10.3%

The degree of deterioration of this deep-frying fat was measured by means of specific resistance as under Example 1.

TABLE 5

| Deep-frying time (X) [hours] | Specific resistance $R \times 10^9$ [$\Omega$] | Conductivity $S \times 10^{-12}$ [$\Omega^- \times cm^{-1}$] | Polar fractions [%] | Acid value [AV] | Relative values [% specific resistance] | | | |
|---|---|---|---|---|---|---|---|---|
| | | | | | 8 hours | | 16 hours | |
| | | | | | linear | log. | linear | log. |
| 0 | 15.89 | 7.17 | 8.7 | 0.10 | — | — | — | — |
| 8 | 11.99 | 9.50 | 0.21 | 100 | 100 | — | — | — |
| 16 | 9.20 | 12.39 | 14.5 | 0.54 | 76.7 | 76.7 | 100 | 100 |
| 20 | 7.89 | 14.44 | 14.3 | 0.56 | 65.8 | 65.8 | 85.7 | 93.0 |
| 24 | 7.37 | 15.57 | 16.5 | 0.84 | 61.0 | 61.0 | 79.5 | 89.7 |
| 28 | 6.32 | 18.03 | 17.8 | 0.78 | 52.7 | 52.7 | 68.7 | 83.0 |
| 30 | 61.3 | 18.59 | 19.4 | 1.10 | 51.1 | 51.1 | 66.6 | 81.7 |

TABLE 5-continued

| Deep-frying time (X) | Specific resistance R × 10⁹ | Conductivity S × 10⁻¹² | Polar fractions | Acid value | Relative values [% specific resistance] | | | |
|---|---|---|---|---|---|---|---|---|
| | | | | | 8 hours | | 16 hours | |
| [hours] | [Ω] | [Ω⁻× cm⁻¹] | [%] | [AV] | linear | log. | linear | log. |
| 32 | 5.81 | 19.62 | 20.0 | 2.20 | 48.4 | 48.8 | 63.1 | 79.2 |
| 34 | 5.40 | 21.11 | 20.4 | 2.70 | 46.0 | 45.0 | 58.6 | 76.0 |
| 38 | 5.39 | 21.15 | 23.0 | 2.85 | 44.9 | 44.9 | 58.5 | 75.9 |
| 40 | 5.11 | 22.30 | 23.4 | 3.27 | 42.6 | 42.6 | 55.5 | 73.5 |
| Gradient (m) | | | | | −1.6 ± 0.16 | −1.0 ± 0.05 | −1.8 ± 0.14 | −1.1 ± 0.07 |
| Axis intercept (b) | | | | | 103 ± 4.0 | 105 ± 1.6 | 123 ± 4.2 | 115 ± 2.1 |
| Correlation coefficient (r) | | | | | −0.9619 | −0.9832 | −0.9693 | −0.9782 |

The best-fit line is given by the equation (see Example 1):

$$y = m \cdot x + b$$

It is clear from Table 5, that the measured values of the specific resistance and of the conductivity are correlated with the degree of deterioration of the deep-frying fat used, which degree of deterioration is expressed by the acid value and the polar fractions. The linear associations between deep-frying fat degree of deterioration and the measured values are also confirmed by the correlation coefficients.

The measured values of the specific resistance and the measured values calculated therefrom of the conductivity and the relative values which were based on the measured values of the deep-frying fat after 8 hours and 16 hours of deep-frying time and were normalized are summarized in Table 6 below:

TABLE 6

| Deep-frying time (X) | Specific resistance R × 10⁹ | Conductivity S × 10⁻¹² | Polar fractions | Acid value | Relative values [% specific resistance] | | | |
|---|---|---|---|---|---|---|---|---|
| | | | | | 8 hours | | 16 hours | |
| [hours] | [Ω] | [Ω⁻× cm⁻¹] | [%] | [AV] | linear | log. | linear | log. |
| 0 | 21.49 | 5.30 | 3.5 | 0.16 | — | — | — | — |
| 8 | 14.68 | 7.76 | 4.4 | 0.44 | 100 | 100 | — | — |
| 16 | 14.51 | 7.85 | 5.5 | 0.55 | 98.84 | 99.58 | 100 | 100 |
| 20 | 12.91 | 8.83 | 11.5 | 0.95 | 87.94 | 95.22 | 86.59 | 94.67 |
| 24 | 12.63 | 9.02 | 15.0 | 1.06 | 86.04 | 94.40 | 78.87 | 93.86 |
| 28 | 10.81 | 10.54 | 16.6 | 1.65 | 73.64 | 88.61 | 72.50 | 88.10 |
| 30 | 10.48 | 10.87 | 16.6 | 1.70 | 71.39 | 87.46 | 70.29 | 86.95 |
| 32 | 9.69 | 11.76 | 20.6 | 1.68 | 66.01 | 84.54 | 64.99 | 84.05 |
| 34 | 8.92 | 12.78 | 22.2 | 1.75 | 60.75 | 81.46 | 59.83 | 80.99 |
| 36 | 8.70 | 13.10 | 21.7 | 2.05 | 59.26 | 80.53 | 58.35 | 80.06 |
| 38 | 8.54 | 13.36 | 21.5 | 2.22 | 58.17 | 79.84 | 57.28 | 79.38 |
| 40 | 8.38 | 13.60 | 22.6 | 2.42 | 57.08 | 79.13 | 56.20 | 78.68 |
| Gradient (m) | | | | | −1.6 ± 0.12 | −0.8 ± 0.06 | −1.9 ± 0.1 | −0.9 ± 0.04 |
| Axis intercept (b) | | | | | 121 ± 3.6 | 1211 ± 1.8 | 127 ± 2.9 | 114 ± 1.2 |
| Correlation coefficient (r) | | | | | −0.9693 | −0.9662 | −0.9864 | −0.9900 |

The best-fit line is given by the equation (see Example 1):

$$y = m \cdot x + b$$

It is clear from Table 6 that the measured values of the specific resistance and of the conductivity are correlated with the degree of deterioration of the deep-frying fat used, which degree of deterioration is expressed by the acid value and the polar fractions. This is also confirmed by the correlation coefficients.

EXAMPLE 5

French fries were deep-fried at 175° C. with a deep-frying fat of the following fatty acid composition
Palmitic acid (C16:0)=6.0%
Stearic acid (C18:0)=7.3%
Oleic acid and oleic acid isomers (C18:1)=73.1%
Linoleic acid and linoleic acid isomers (C18:2)=6.8%

The degree of deterioration of this deep-frying fat was measured by means of specific resistance as shown in Example 1.

EXAMPLE 6

Neck of pork was deep-fried at 175° C. with a deep-frying fat of the following fatty acid composition Palmitic acid (C16:0)=6.8%
Stearic acid (C18:0)=6.7%
Oleic acid and oleic acid isomers (C18:1)=71.5%
Linoleic acid and linoleic acid isomers (C18:2)=6.3%

The degree of deterioration of this deep-frying fat was measured by means of specific resistance as under Example 1.

The measured values of the specific resistance and the measured values calculated therefrom of the conductivity and the relative values which were based on the measured values of the deep-frying fat after 8 hours and 16 hours of deep-frying time and were normalized are summarized in Table 7 below:

TABLE 7

| Deep-frying time (X) | Specific resistance $R \times 10^9$ | Conductivity $S \times 10^{-12}$ | Polar fractions | Acid value | Relative values [% specific resistance] | | | |
|---|---|---|---|---|---|---|---|---|
| | | | | | 8 hours | | 16 hours | |
| [hours] | [Ω] | [Ω⁻¹ × cm⁻¹] | [%] | [AV] | linear | log. | linear | log. |
| 0 | 11.14 | 10.23 | 3.1 | 0.16 | — | — | — | — |
| 8 | 9.13 | 12.48 | 3.9 | 0.53 | 100 | 100 | — | — |
| 16 | 7.21 | 15.81 | 6.6 | 0.72 | 78.97 | 89.32 | 100 | 100 |
| 20 | 6.77 | 16.83 | 6.7 | 0.76 | 74.15 | 86.48 | 93.90 | 96.81 |
| 24 | 5.97 | 19.09 | 9.2 | 1.63 | 65.39 | 80.79 | 82.80 | 90.45 |
| 28 | 5.83 | 19.55 | 10.4 | 1.85 | 58.27 | 75.58 | 73.79 | 89.33 |
| 30 | 5.09 | 22.39 | 12.3 | 1.83 | 55.75 | 73.58 | 70.60 | 82.37 |
| 32 | 4.80 | 23.75 | 12.8 | 1.78 | 52.57 | 70.93 | 66.57 | 79.40 |
| 34 | 4.30 | 26.51 | 12.8 | 1.78 | 47.10 | 65.95 | 59.64 | 73.84 |
| 36 | 3.80 | 30.00 | 12.4 | 1.74 | 41.67 | 60.36 | 52.70 | 64.58 |
| 38 | 3.55 | 32.11 | 13.0 | 1.76 | 38.88 | 57.29 | 49.24 | 61.65 |
| 40 | 3.38 | 33.71 | 13.4 | 1.83 | 37.02 | 55.07 | 46.88 | |
| Gradient (m) | | | | | $-1.9 \pm 0.05$ | $-1.4 \pm 0.06$ | $-2.3 \pm 0.06$ | $-1.6 \pm 0.08$ |
| Axis intercept (b) | | | | | $112 \pm 1.5$ | $113 \pm 1.8$ | $138 \pm 1.9$ | $129 \pm 2.6$ |
| Correlation coefficient (r) | | | | | −0.9955 | −0.9881 | −0.9958 | −0.9857 |

The best-fit line is given by the equation (see Example 1):

$$y = m \cdot x + b$$

It is clear from Table 7 that the measured values of the specific resistance and of the conductivity are correlated with the degree of deterioration of the deep-frying fat used, which degree of deterioration is expressed by the acid value and the polar fractions. This is also confirmed by the correlation coefficients.

Other embodiments of the invention will become apparent to those skilled in the art from consideration of the specification and practice of the invention disclosed herein. It is intended that the specification be considered as exemplary only, with the true scope and spirit of the invention being indicated by the following claims.

What is claimed is:

1. A method for determining the degree of deterioration of oils or fats used in a process for frying foods and/or the frying time at which the oil or fat is no longer usable, which comprises:
   applying a direct current voltage to the frying oils and fats,
   measuring the specific electrical resistance of the frying oils or fats at different frying times, and
   determining the degree of deterioration and/or the frying time at which the oil or fat is no longer usable by a first correlation between the decrease of the resistance with increasing frying time and a second correlation between the specific resistance and the degree of deterioration.

2. A method as claimed in claim 1, wherein the first correlation is based on the difference between a first specific resistance measured any time prior to a first use of the fat or oil in the frying process and a second specific resistance measured at at least one predetermined time point after the first use.

3. A method as claimed in claim 2, wherein a linear function based on the difference in the first and second resistances measured at the time prior to first use and the one predetermined time point respectively, is extrapolated to a time point at which the oil or fat is no longer usable.

4. A method as claimed in claim 2, further comprising, normalizing the first measured specific resistance value as 100% specific resistance, and subsequently dividing said normalized value by the quotient of said first measured specific resistance divided by the measured specific resistance at the at least one predetermined time point to produce a percentage specific resistance at the at least one predetermined time point.

5. A method as claimed in claim 4, further comprising, using the least squares method, with the frying time as the x-axis and the specific resistance percentage as the y-axis, to determine the slope (m) and y-intercept (b) of the best fit line represented by the slope-intercept equation:

$$y = mx + b$$

wherein m is equal to the slope of the line, and b is equal to the y-intercept of the line.

6. A method as claimed in claim 5, further comprising using the slope-intercept equation and the second correlation to determine the degree of deterioration at any selected time.

7. A method as claimed in claim 1, wherein the specific resistance is the ohmic resistance of the fat or oil in a measurement cell, which cell is defined by a cell constant c which is the ratio between the electrode spacing d (cm) and the electrode surface area F (cm).

8. A method as claimed in claim 7, wherein said cell is a test tube having about a 20 mm diameter.

9. A method as claimed in claim 7, further comprising placing a fat or oil sample in said cell, and heating said cell prior to said measuring.

10. A method as claimed in claim 9, further comprising placing two flat platinum electrodes in said cell and applying about 100 volts therebetween prior to said measuring.

11. A method as claimed in claim 10, wherein said measuring further comprises measuring the specific resistance after the voltage has been applied for about one minute.

12. A method as claimed in claim 1, wherein the first correlation used is the difference between a first specific resistance measured at a first predetermined time point after a first use of the oil or fat in the frying process and a second specific resistance measured at at least one additional predetermined time point after the first predetermined time point.

13. A method as claimed in claim 12, wherein the first predetermined time point is about 4 to about 16 hours after the first use of the oil or fat in the frying process.

14. A method as claimed in claim 12, wherein a linear function based on the difference in the first and second resistances measured at the first predetermined time point and additional predetermined time point respectively, is extrapolated to a time point at which the oil or fat is no longer usable.

15. A method as claimed in claim 12, wherein said measuring further comprises measuring the first specific resistance value at said first predetermined time point after the first use of the fat or oil, and measuring the specific resistance at the at least one additional predetermined time point after the first predetermined time point.

16. A method as claimed in claim 15, further comprising, normalizing the first measured specific resistance value as 100%, and subsequently dividing said normalized value by the quotient of said first measured specific resistance divided by the measured specific resistance at the at least one additional predetermined time point to produce a specific resistance percentage at the at least one additional predetermined time point.

17. A method as claimed in claim 16, further comprising, using the least squares method, with the frying time as the x-axis and the specific resistance percentage as the y-axis, to determine the slope (m) and y-intercept (b) of the best fit line represented by the equation:

$$y=mx+b$$

wherein m is equal to the slope of the line, and b is equal to the y-intercept of the line.

18. A method as claimed in claim 17, further comprising using the slope-intercept equation and the second correlation to determine the degree of deterioration at any selected time.

* * * * *